United States Patent
Kusaka et al.

(10) Patent No.: US 10,501,586 B2
(45) Date of Patent: Dec. 10, 2019

(54) POLYESTER-BASED RESIN PARTICLES, PROCESS FOR PRODUCING SAME, AND USE THEREOF

(71) Applicant: SEKISUI PLASTICS CO., LTD., Osaka (JP)

(72) Inventors: Akiyoshi Kusaka, Nara (JP); Kaori Kuwagaki, Nara (JP); Ryosuke Harada, Shiga (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 43 days.

(21) Appl. No.: 15/746,153

(22) PCT Filed: Aug. 18, 2016

(86) PCT No.: PCT/JP2016/074139
§ 371 (c)(1),
(2) Date: Jan. 19, 2018

(87) PCT Pub. No.: WO2017/056773
PCT Pub. Date: Apr. 6, 2017

(65) Prior Publication Data
US 2018/0208721 A1 Jul. 26, 2018

(30) Foreign Application Priority Data

Sep. 28, 2015 (JP) ................. 2015-189928

(51) Int. Cl.
| | | |
|---|---|---|
| C08J 3/12 | (2006.01) | |
| A61Q 1/12 | (2006.01) | |
| A61K 8/85 | (2006.01) | |
| C09D 7/40 | (2018.01) | |
| A61K 8/02 | (2006.01) | |
| A61Q 19/00 | (2006.01) | |
| C08G 63/183 | (2006.01) | |

(52) U.S. Cl.
CPC ............... *C08J 3/12* (2013.01); *A61K 8/0241* (2013.01); *A61K 8/85* (2013.01); *A61Q 1/12* (2013.01); *A61Q 19/007* (2013.01); *C08G 63/183* (2013.01); *C09D 7/69* (2018.01); *A61K 2800/412* (2013.01); *C08J 2367/02* (2013.01)

(58) Field of Classification Search
USPC ......................... 528/271, 272, 279
See application file for complete search history.

(56) References Cited

U.S. PATENT DOCUMENTS

| | | | |
|---|---|---|---|
| 6,130,281 | A | 10/2000 | Seo et al. |
| 2006/0046004 | A1 | 3/2006 | Ekart et al. |
| 2014/0213753 | A1 | 7/2014 | Bashir |

FOREIGN PATENT DOCUMENTS

| | | | |
|---|---|---|---|
| EP | 0376653 | A | 7/1990 |
| JP | S62-197424 | A | 9/1987 |
| JP | 2-215838 | A | 8/1990 |
| JP | 06-263882 | A | 9/1994 |
| JP | 10-231446 | A | 9/1998 |
| JP | 11-114961 | A | 4/1999 |
| JP | 2006-328251 | A | 12/2006 |
| JP | 2007-332365 | | 12/2007 |
| JP | 2008-063305 | A | 3/2008 |
| JP | 2008-511731 | A | 4/2008 |
| JP | 2011-218717 | A | 11/2011 |
| JP | 2014-166965 | A | 9/2014 |
| WO | 2006/028748 | A2 | 3/2006 |

OTHER PUBLICATIONS

International Search Report issued with respect to Patent Application No. PCT/JP2016/074139, dated Oct. 11, 2016.
Extended European Search Report in EP Patent Application No. 16850949, dated May 8, 2019.

*Primary Examiner* — Terressa Boykin
(74) *Attorney, Agent, or Firm* — Greenblum & Bernstein, P.L.C.

(57) ABSTRACT

Polyester-based resin particles including a polyester-based resin as a base resin, in which the base resin exhibits a plurality of endothermic peaks corresponding to crystal melting temperatures by DSC measurement, at least one of the endothermic peaks exists in each region of a low temperature side region and a high temperature side region, a maximum endothermic peak of the low temperature side region and a maximum endothermic peak of the high temperature side region exhibit a crystal melting heat amount ratio (low temperature side crystal melting heat amount/high temperature side crystal melting heat amount) in a range of 0.1 to 1.5, and the polyester-based resin particles have a volume average particle diameter of 1 to 50 μm.

7 Claims, 5 Drawing Sheets

POLYESTER-BASED RESIN PARTICLES, PROCESS FOR PRODUCING SAME, AND USE THEREOF

TECHNICAL FIELD

The present invention relates to polyester-based resin particles, a process (method) for producing the same and use thereof. More particularly, the present invention relates to polyester-based resin particles having the fine particle diameter and use thereof, and a method for easily producing polyester-based resin particles by mechanical grinding from a polyester-based raw material resin. The polyester-based resin particles of the present invention are suitable for an additive for coating, an additive for a cosmetic material, and the like.

BACKGROUND TECHNOLOGY

Resin particles composed of a radical polymerization product of a vinyl-based monomer are usually produced by a suspension polymerization method, an emulsion polymerization method or the like, and relatively fine particles can be produced. The resulting resin particles are widely used as an additive for coating, an additive for a cosmetic material or the like.

On the other hand, resin particles composed of a polycondensate of a polyester-based resin, a polyamide-based resin, a polycarbonate-based resin, a fluorine-based resin or the like are mainly produced by a mechanical grinding method or a freeze grinding method. It is however known that it is generally difficult to produce fine particles by these methods. As a method for producing fine polyester-based resin particles among resin particles of these polycondensates, the following three methods have been proposed.

First is a method described in Japanese Unexamined Patent Application, First Publication No. Hei 2-215838 (Patent Document 1), and this is a method of obtaining fine polyester-based resin particles of about several micrometers to several tens of micrometers by heating a mixture consisting of a partially crystalline polyester and an intermediate solvent thereof to a melting point of the mixed state or higher, and thereafter, cooling the mixture to a temperature at which solid phase/liquid phase separation is generated.

Second is a method described in Japanese Unexamined Patent Application. First Publication No. 2006-328251 (Patent Document 2), and this is a method of obtaining fine polyester-based resin particles of 0.1 to 50 μm by grinding porous pellets which are obtained by partially depolymerizing a polyester-based resin using glycol.

Third is a method described in Japanese Unexamined Patent Application, First Publication No. Hei 11-114961 (Patent Document 3), and this is a method of obtaining polyester-based resin particles by heat-treating a PET resin as a raw material, thereby bring it into the crystal state where the crystallization degree is 55% or more and an area of a high temperature side second peak region adjacent to a first peak region, which is detected by DSC analysis, has been increased, and thereafter, mechanically grinding the crystal under an ambient temperature.

PRIOR ART DOCUMENTS

Patent Documents

Patent Document 1: Japanese Unexamined Patent Application, First Publication No. Hei 2-215838

Patent Document 2: Japanese Unexamined Patent Application, First Publication No. 2006-328251

Patent Document 3: Japanese Unexamined Patent Application, First Publication No. Hei 11-114961

SUMMARY OF THE INVENTION

Problem to be Solved by the Invention

Since the method of Patent Document 1 needs warming to a temperature exceeding the melting temperature of the polyester-based resin (for example, 200° C. or higher in polyethylene terephthalate), there was a problem that the producing cost is high. Additionally, there was a problem that troublesome treatment of extracting the intermediate solvent is necessary in a step of purifying particles, and the production efficiency is reduced. In addition, even by having passing through the method having these problems, there was limitation that only porous shaped particles are obtained.

Meanwhile, in the method of Patent Document 2, to make grinding easy, porous pellets are formed by partial depolymerization. Since it is, however, apprehended in this method that byproducts (for example, terephthalic acid ester) which are generated at the time of partial depolymerization remain, there was a problem that utility is limited. Additionally, there was a problem that troublesome treatment of partial depolymerization is necessary, and the production efficiency is reduced.

The method of Patent Document 3 makes grinding at an ambient temperature easy, without using a method such as freeze-grinding and the like which are generally used in grinding resins, by improving the crystallization degree to 55% or more by heat treatment, and changing the crystal state. In this method, even when heat treatment for a long time (a heating time necessary for changing a crystal phase is usually 3 to 40 hours) is performed, fine grinding below 50 μm cannot be performed. For that reason, even when grinding is repeated, only fine particles of at most about 85 μm are obtained. Additionally, since the crystallization degree of the resulting particles has been improved considerably (55% or more) from that of a raw material resin, there was a problem that, for example, when the particles are used in a generally used powder paint, meltability of particles at the time of baking is reduced. Furthermore, in painting material and other miscellaneous applications, a problem from a view point of physical properties, such as reduction in the strength of particles themselves (brittleness) due to too high crystallizability and the like remains.

Means for Solving the Problem

The inventors of the present invention found out that polyester-based resin particles having two endothermic peaks exhibiting a crystal melting heat amount ratio in a specific range by DSC measurement, and the volume average particle diameter in a specific range, can solve the above-mentioned problems, and arrived at the present invention.

Thus, according to the present invention, there are provided polyester-based resin particles comprising a polyester-based resin as a base resin,
wherein
the base resin exhibits a plurality of endothermic peaks corresponding to crystal melting temperatures by DSC measurement, at least one of the endothermic peaks exists in each region of a low temperature side region and a high temperature side region, a maximum endothermic peak of the low temperature side region and a maximum endothermic peak of the high temperature side region exhibit a crystal melting heat amount ratio (low temperature side crystal melting heat amount/high temperature side crystal melting heat amount) in a range of 0.1 to 1.5, and the polyester-based resin particles have a volume average particle diameter of 1 to 50 µm.

Furthermore, according to the present invention, there is provided a method for producing the polyester-based resin particles, the method comprising the steps of:

contacting a polyester-based raw material resin having an intrinsic viscosity of 0.5 to 1.3 dl/g and a crystallization degree by DSC measurement of 30 to 50% with a glycol ether-based solvent; and grinding a mixture after the contact, wherein the contact is performed under a temperature of the crystallization temperature of the polyester-based raw material resin or higher, and the glycol ether-based solvent is 3-methoxy-3-methyl-1-butanol.

Additionally, according to the present invention, there is provided a coating material comprising the polyester-based resin particles.

Furthermore, according to the present invention, there is provided a cosmetic material comprising the polyester-based resin particles.

Effects of Invention

According to the present invention, there can be provided polyester-based resin particles having the fine particle diameter, without considerably changing the crystallization degree from that of a raw material resin.

In any of the following cases, there can be provided finer polyester-based resin particles, without considerably changing the crystallization degree from that of a raw material resin.

(1) The polyester-based resin is polyethylene terephthalate.
(2) The maximum endothermic peak of the low temperature side region exhibits a maximum peak value at a range of 230° C. or higher and lower than 250° C., and the maximum endothermic peak of the high temperature side region exhibits a maximum peak value at a range of higher than 250° C. and 260° C. or lower.
(3) The maximum endothermic peak of the low temperature side region exhibits a crystal melting heat amount of 5 to 35 J/g, and the maximum endothermic peak of the high temperature side region exhibits a crystal melting heat amount of 20 to 50 J/g.

Additionally, according to the present invention, there can be provided a production method by which the above-mentioned polyester-based resin particles can be prepared by a simple fine grinding method.

BEST MODE FOR CARRYING OUT THE INVENTION (Polyester-Based Resin Particles)

Polyester-based resin particles contain a polyester-based resin as a base resin, and have the following various physical properties.

(1) Various Physical Properties (a) Crystal Melting Heat Amount Ratio of Base Resin A maximum endothermic peak of a low temperature side region and a maximum endothermic peak of a high temperature side region exhibit a crystal melting heat amount ratio (low temperature side crystal melting heat amount/high temperature side crystal melting heat amount) in a range of 0.1 to 1.5.

Herein, the endothermic peak is a peak corresponding to the crystal melting temperature which is shown by DSC measurement of a base resin. The base resin exhibits a plurality of endothermic peaks. Additionally, the low temperature side region and the high temperature side region are regions having a boundary at 250° C., and at least one endothermic peak exists in each region.

When the crystal melting heat amount ratio is less than 0.1, and when the ratio is greater than 1.5, sufficient fine grindability is not shown. The crystal melting heat amount ratio can take 0.1, 0.12, 0.13, 0.15, 0.18, 0.3, 0.5, 0.8, 1.0, 1.2, 1.3, 1.4, 1.45, and 1.5. The crystal melting heat amount ratio is preferably 0.12 to 1.45, and more preferably 0.13 to 1.40.

Additionally, it is preferable that the maximum endothermic peak of the low temperature side region exhibits a maximum peak value at a range of 230° C. or higher and lower than 250° C. On the other hand, it is preferable that the maximum endothermic peak of the high temperature side region exhibits a maximum peak value at a range of higher than 250° C. and 260° C. or lower. By having the maximum peak value in these ranges, the nature of fine grindability can be imparted without changing crystallizability of the base resin. The maximum endothermic peak of the low temperature side region can take 230° C., 235° C., 240° C. 245° C. and 249° C. On the other hand, the maximum endothermic peak of the high temperature side region can take 251° C., 253° C., 255° C., 257° C., and 260° C.

Furthermore, it is preferable that the maximum endothermic peak of the low temperature side region exhibits a crystal melting heat amount of 5 to 35 J/g. On the other hand, it is preferable that the maximum endothermic peak of the high temperature side region exhibits a crystal melting heat amount of 20 to 50 J/g. By the crystal melting heat amount being in these ranges, the nature of fine grindability can be imparted to the base resin. The maximum endothermic peak of the low temperature side region can take 5 J/g, 10 J/g, 15 J/g, 20 J/g, 25 J/g, 30 J/g, and 35 J/g. On the other hand, the maximum endothermic peak of the high temperature side region can take 20 J/g, 25 J/g, 30 J/g, 35 J/g, 40 J/g, 4.5 J/g, and 50 J/g.

(b) Volume Average Particle Diameter

Polyester-based resin particles have a volume average particle diameter of 1 to 50 μm. When the volume average particle diameter is less than 1 μm, it is also not easy to obtain particles having such a diameter in the production method of the present invention. When the volume average particle diameter is greater than 50 μm, since particles can be obtained by a method other than a method explained below, merits of the present invention may be reduced. The volume average particle diameter can take 1 μm, 10 μm, 15 μm, 20 μm, 25 μm, 30 μm, 35 μm, 40 μm, 45 μm, and 50 μm. Depending on utility, the volume average particle diameter is preferably 1 to 45 μm, and more preferably 1 to 40 pin.

(c) Outer Shape

An outer shape of polyester-based resin particles is not particularly limited. Examples thereof include a spherical shape, a columnar shape, an undefined shape, and the like. Among them, it is preferable that the outer shape is as near a spherical shape as possible.

(2) Base Resin

It is preferable that the polyester based resin as the base resin is polyethylene terephthalate.

Herein, it is preferable that polyethylene terephthalate is composed of specifically 90 mol % or more, preferably 95 mol % or more, and further preferably 98 mol % or more of an ethylene terephthalate unit. Examples of another component include acid components such as isophthalic acid, naphthalenedicarboxylic acid, and sebacic acid, and glycol components such as diethylene glycol and propylene glycol. Further specifically, examples thereof include an ethylene isophthalate unit, an ethylene naphthalene dicarboxylate unit, a diethylene terephthalate unit, and the like. That is, a raw material, polyethylene terephthalate, is preferably a homopolymer, and may be a copolymer using a dicarboxylic acid component other than terephthalic acid such as isophthalic acid and naphthalenedicarboxylic acid and/or a glycol component other than ethylene glycol such as diethylene glycol, at 10 mol % or less based on total dicarboxylic acid components. Alternatively, a raw material, polyethylene terephthalate, may be a blend polymer in which other condensation resins are mixed therein at 10% by mass or less based on the total mass.

Alternatively, polyethylene terephthalate obtained by using monoethylene glycol which was synthesized employing plant-derived bioethanol as a raw material can also be used.

It is preferable that the polyester-based resin has an intrinsic viscosity of 0.5 to 1.3 dl/g. When the intrinsic viscosity is less than 0.5 dl/g, since the molecular weight is low, the polyester-based resin may not have sufficient resin physical properties. When the intrinsic viscosity is greater than 1.3 dl/g, even if the production method of the present invention is used, a long solvent contacting time necessary for easy grinding may become necessary. The intrinsic viscosity can take 0.5 dl/g, 0.6 dl/g, 0.7 dl/g, 0.9 dl/g, 1.0 dl/g, 1.1 dl/g, 1.2 dl/g, and 1.3 dl/g. The intrinsic viscosity is more preferably 0.6 to 1.2 dl/g, and further preferably 0.7 to 1.1 dl/g.

(3) Other Additives

The polyester-based resin particles may contain other additives in addition to the base resin, as necessary Examples of other additives include a plasticizer, a flame retardant, an auxiliary flame retardant, an antistatic agent, a spreading agent, an air bubble adjusting agent, a filler, a coloring agent, a weather resistant agent, an anti-aging agent, a lubricant, an anti-fogging agent, a perfume, and the like.

(Method for Producing Polyester-Based Resin Particles)

A method for producing the above-mentioned polyester-based resin particles includes the steps of contacting a polyester-based raw material resin having an intrinsic viscosity of 0.5 to 1.3 dl/g and a crystallization degree by DSC measurement of 35 to 50% with a glycol ether-based solvent (contacting step), and grinding the mixture after the contact (grinding step). A shape of the polyester-based raw material resin used herein is not particularly limited. For example, a commonly used resin having a so-called pellet-like shape having a diameter and length of about 1 to several millimeters can be suitably used.

The intrinsic viscosity can take 0.5 dl/g, 0.6 dl/g, 0.7 dl/g, 0.9 dl/g, 1.0 dl/g, 1.1 dl/g, 1.2 dl/g, and 1.3 dl/g. The crystallization degree can take 35%, 37%, 40%, 43%, 45%, 47%, and 50%.

(1) Contacting Step

Contact is normally performed under a temperature of the crystallization temperature of the polyester-based raw material resin or higher. By contacting under this temperature, reduction in the intrinsic viscosity can be effectively performed. A contact temperature is preferably higher than the crystallization temperature by 20° C. or more, more specifically, is more preferably higher in a range of 25 to 60° C., and may be higher by 25° C., 30° C., 35° C., 40° C., 45° C., 50° C., 55° C., or 60° C. Herein, when a polyethylene terephthalate resin is used, it is known that the resin usually has the crystallization temperature at around 140° C., and accordingly, a preferable range of the contact temperature is in a range of 165 to 200° C. After contact, the resin is usually cooled to room temperature (about 25° C.).

In a contacting step, the polyester-based resin is warmed to a temperature of the crystallization temperature of the polyester-based resin or higher in the presence of a glycol ether-based solvent, and thereafter, is cooled. By this series of procedures, the polyester-based raw material resin can be made to have the low intrinsic viscosity without generating partial depolymerization to a monomer level, and the crystal melting peak temperature by DSC measurement can be elevated without greatly changing the crystallization degree of the polyester-based resin. The inventors think that the reason of this elevation is crystal growth due to rearrangement of crystals, and this elevation can change the mechanical strength, to make mechanical grinding easy. In addition, the inventors confirmed in Examples that conversion into porousness as described in Patent Document 2 has not been generated, by electron microscopic observation of the polyester-based raw material resin after the contacting step. Accordingly, the inventors think that the production method of the present invention does not utilize easy grindability due to reduction in the strength of pellets by dissolution of low molecular weight components due to partial depolymerization. Additionally, since there is little change in the crystallization degree, and increase in the specific gravity before and after the contacting step is not observed, the inventors think that the reason is not easy grindability due to increase in the crystallization degree.

The polyester-based raw material resin before contacting with the glycol ether-based solvent has the intrinsic viscosity and the crystallization degree in the above-mentioned ranges.

When the intrinsic viscosity is less than 0.5 dl/g, reduction in the molecular weight due to contact with the glycol-based solvent is remarkable, and resin particles which are obtained by grinding may not have sufficient resin physical properties. When the intrinsic viscosity is greater than 1.3 dl/g, even if the production method of the present invention is used, a long solvent contacting time necessary for easy grinding may become necessary. The intrinsic viscosity is more preferably 0.6 to 1.3 dl/g, and further preferably 0.7 to 1.1 dl/g. The crystallization degree is more preferably 35 to 50%, and further preferably 35 to 45%. When the crystallization degree is less than 30%, the grinding effect is not sufficient due to elasticity of the resin, and fine grinding may become difficult, such as conversion into thread-like particles. When the crystallization degree is greater than 50%, the improving effect by solvent contact is hardly obtained due to high crystallizability.

As the glycol ether-based solvent, 3-methoxy-3-methyl-1-butanol can be used.

Contact is enough if a total surface of the polyester-based raw material resin which is desired to be contacted comes in contact with the glycol ether-based solvent. Accordingly, contact may be performed by a method of immersing the polyester-based raw material resin in the glycol ether-based solvent filled in a container, a method of spraying the glycol ether-based solvent on the polyester-based raw material resin or the like. Among them, the former immersion method is preferable from a view point that contact is surely performed.

The polyester-based raw material resin after contact may be subjected to a step of filtering from the glycol ether-based solvent, a water washing step, and a drying step, as necessary.

(2) Grinding Step

Grinding is not particularly limited, as far as polyester-based resin particles can be obtained from the polyester-based raw material resin after contact. Any of methods using various mills can be used in a grinding method.

In the grinding step, after coarse grinding with a grinding machine such as a crusher, a hammer mill, and a feather mill, furthermore, fine grinding can be performed, for example, with a mechanical grinding machine such as a KRYPTRON system (manufactured by Kawasaki Heavy Industries, Ltd.). Super Rotor (manufactured by Nisshin Engineering Inc.), Turbo-Mill (manufactured by Turbo Kogyo Co., Ltd.), and a pulverizer (manufactured by Hosokawa Micron Corporation), or a fine grinding machine by an air jet system of a current jet mill, Super Jet Mill (manufactured by Nisshin Engineering Inc.).

Thereafter, furthermore, as necessary, classification can be performed using a classifying machine or a sieving machine such as Elbow Jet of an inertial classification system (manufactured by Nittetsu Mining Co., Ltd.), Turboplex of a centrifugal classification system (manufactured by Hosokawa Micron Corporation), TSP Separator (manufactured by Hosokawa Micron Corporation), and FACULTY (manufactured by Hosokawa Micron Corporation) to obtain objective polyester-based resin particles.

Alternatively, as necessary, after grinding, spheroidizing treatment and the like can also be performed using Hybridization System (manufactured by Nara Machinery Co., Ltd.), MECHANO FUSION System (manufactured by Hosokawa Micron Corporation), Faculty (manufactured by Hosokawa Micron Corporation) or Meteorainbow MR Type (manufactured by Nippon Pneumatic Mfg. Co., Ltd.).

It is preferable that the polyester-based resin particles which are obtained by grinding are such that a maximum endothermic peak of the low temperature side region and a maximum endothermic peak of the above-mentioned high temperature side region exhibit a crystal melting heat amount ratio (low temperature side crystal melting heat amount/high temperature side crystal melting heat amount) in a range of 0.1 to 1.5, and exhibit the intrinsic viscosity which is 30 to 100% of that of the polyester-based raw material resin. By change of the intrinsic viscosity and crystallizability into these ranges, the mechanical strength of the polyester-based raw material resin can be made to be changed, to easily perform mechanical grinding. The crystal melting heat amount ratio can take 0.1, 0.3, 0.5, 0.8, 1.0, 1.3, and 1.5. The intrinsic viscosity of the polyester-based resin particles which are obtained by grinding can take 30%, 40%, 50%, 60%, 70%, 80%, 90%, and 100% of the intrinsic viscosity of the polyester-based raw material resin.

The polyester-based resin particles which are obtained by grinding may be classified into desired particle diameters, as necessary.

(Utility)

The polyester-based resin particles can be used in utility such as a coating material and a cosmetic material.

(1) Coating Material

The coating material contains a binder resin, an ultraviolet curing resin, a solvent, and the like, as necessary. As the binder resin, a resin which is soluble in an organic solvent or water, or an emulsion-type aqueous resin which can be dispersed in water can be used.

Examples of the binder resin include an acrylic resin, an alkyd resin, a polyester resin, a polyurethane resin, a chlorinated polyolefin resin, an amorphous polyolefin resin, and the like, and examples of the ultraviolet curing resin include polyfunctional (meth)acrylate resins such as polyhydric alcohol polyfunctional (meth)acrylate; polyfunctional urethane acrylate resins such as a resin which is synthesized from a diisocyanate, a polyhydric alcohol, and a (meth) acrylic acid ester having a hydroxy group; and the like.

As the ultraviolet curing resin, a polyfunctional (meth) acrylate resin is preferable, and a polyhydric alcohol polyfunctional (meth)acrylate resin having 3 or more (meth) acryloyl groups in a molecule is more preferable. Specifically, examples of the polyhydric alcohol polyfunctional (meth)acrylate resin having 3 or more (meth)acryloyl groups in a molecule include trimethylolpropane tri(meth) acrylate, trimethylolethane tri(meth)acrylate, 1,2,4-cyclohexane tetra(meth)acrylate, pentaglycerol triacrylate, pentaerythritol tetra(meth)acrylate, pentaerythritol tri(meth) acrylate, dipentaerythritol triacrylate, dipentaerythritol pentaacrylate, dipentaerythritol tetra(meth)acrylate, dipentaerythritol hexa(meth)acrylate, tripentaerythritol triacrylate, tripentaerythritol hexaacrylate, and the like, and they may be used alone, or two or more may be used together.

When the ultraviolet curing resin is used, a photopolymerization initiator is added to the ultraviolet curing resin to form a binder resin. The photopolymerization initiator is not particularly limited.

Examples of the photopolymerization initiator include acetophenones, benzoins, benzophenones, phosphine oxides, ketals, α-hydroxyalkylphenones, α-aminoalkylphenone, anthraquinones, thioxanthones, an azo compound, peroxides (described in Japanese Unexamined Patent Application. First Publication No. 2001-139663 and the like), 2,3-dialkyldione compounds, disulfide compounds, fluoroamine compounds, aromatic sulfoniums, onium salts, a borate salt, an active halogen compound, α-acyloxime ester, and the like.

These binder resins or ultraviolet curing resins can be appropriately selected depending on adherability of paint to a substrate to be coated, the environment under which they are used, and the like.

Addition amounts of the binder resin or the ultraviolet curing resin and the polyester-based resin particles are also different depending on the film thickness of a formed coated film, the average particle diameter of the polyester-based resin particles, and a coating method. An addition amount of the binder resin is preferably 5 to 50% by mass based on a total of the binder resin (solid content when an emulsion-type aqueous resin is used) and the polyester-based resin particles. The more preferable content is 10 to 50% by mass, and the further preferable content is 20 to 40% by mass.

The solvent is not particularly limited, but it is preferable to use a solvent which can dissolve or disperse the hinder resin or the ultraviolet curing resin. For example, in the case of an oil-based paint, examples of the solvent include hydrocarbon-based solvents such as toluene and xylene; ketone-based solvents such as methyl ethyl ketone and methyl isobutyl ketone; ester-based solvents such as ethyl acetate and butyl acetate; ether-based solvents such as dioxane, ethylene glycol diethyl ether, and ethylene glycol monobutyl ether; and the like. In the case of a water-based paint, water, alcohols, and the like can be used. These solvents may be used alone, or two or more may be used by mixing them. The solvent content in the coating material is usually about 20 to 60% by mass based on a total amount of a paint composition.

The coating material may contain the known painted surface adjusting agent, flowability adjusting agent, ultraviolet absorbing agent, light stabilizer, curing catalyst, extender pigment, coloring pigment, metal pigment, mica powder pigment, dye, and the like, as necessary.

A method of forming a coated film using the coating material is not particularly limited, but any of the known methods can be used. Examples thereof include a spray painting method, a roll painting method, a brushing method, and the like, and to coat a substrate such as a film as a thin layer, examples thereof include a coating reverse roll coating method, a gravure coating method, a die coating method, a comma coating method, and a spray coating method A paint composition may be diluted as necessary to adjust the viscosity. Examples of a diluent include hydrocarbon-based solvents such as toluene and xylene; ketone-based solvents such as methyl ethyl ketone and methyl isobutyl ketone; ester-based solvents such as ethyl acetate and butyl acetate; ether-based solvents such as dioxane and ethylene glycol diethyl ether, water; alcohol-based solvents; and the like. These diluents may be used alone, or may be used by mixing two or more of them.

A coated film can be formed by coating an arbitrary coating surface of a substrate or the like to prepare a coating film, drying this coating film, and thereafter, curing the coating film, as necessary. In addition, a coated film using the coating material is used in various substrates as a coating, and the substrate is a metal, a timber, a glass, a plastic or the like, without particular limitation. Alternatively, the coated film can also be used by coating on a transparent substrate such as PET, PC, and acryl.

(Cosmetic Material)

It is preferable that a cosmetic material contains the polyester-based resin particles in a range of 1 to 40% by mass.

Examples of the cosmetic material include cleaning cosmetics such as a soap, a body shampoo, a cleansing cream, and a facial scrub; body cosmetic materials such as a skin lotion, a cream, a milky lotion, packs, a face powder, a foundation, a lipstick, a lip cream, a cheek rouge, an eyebrow cosmetic, a manicure cosmetic, a hair washing cosmetic, a hair dye, a hairdressing, an aromatic cosmetic, a tooth paste, a bath agent, an antiperspirant, a sunscreen product, a suntan product, a body powder, and a baby powder; lotions such as a shaving cream, a pre-shave lotion, an after shave lotion, and a body lotion; and the like.

Additionally, an ingredient which is generally used in a cosmetic material can be blended depending on the purpose, in such a range that the effect of the present invention is not deteriorated. Examples of such an ingredient include water, a lower alcohol, a fat and oil and waxes, a hydrocarbon, a higher fatty acid, a higher alcohol, a sterol, a fatty acid ester, a metal soap, a moisturizing agent, a surfactant, a polymer compound, a coloring material raw material, a perfume, an antiseptic and bactericide, an antioxidant, an ultraviolet absorbing agent, and a special blending ingredient.

Examples of the fat and oil and waxes include an avocado oil, an almond oil, an olive oil, cacao butter, beef tallow, a sesame oil, a wheat germ oil, a safflower oil, shea butter, a turtle oil, a *camellia* oil, a persic oil, a castor oil, a grape oil, a macadamia nut oil, a mink oil, an egg-yolk oil, Japan wax, a palm oil, a rose hip oil, a hardened oil, a silicone oil, an orange raffia oil, carnauba wax, candelilla wax, whale wax, jojoba oil, montan wax, beeswax, lanolin, and the like.

Examples of the hydrocarbon include liquid paraffin, vaseline, paraffin, ceresin, microcrystalline wax, squalene, and the like. Examples of the higher fatty acid include lauric acid, myristic acid, palmitic acid, stearic acid, oleic acid, behenic acid, undecylenic acid, oxystearic acid, linolic acid, lanolin fatty acid, and synthetic fatty acid.

Examples of the higher alcohol include lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, isostearyl alcohol, jojoba alcohol, decyltetradecanol, and the like.

Examples of the sterol include cholesterol, dihydrocholesterol, phytocholesterol, and the like. Examples of the fatty acid ester include ethyl linoleate, isopropyl myristate, lanolin fatty acid isopropyl, hexyl laurate, myristyl myristate, cetyl myristate, octyldodecyl myristate, decyl oleate, octyldodecyl oleate, hexadecyl dimethyloctanoate, cetyl isoocтanoate, decyl palmitate, trimyristic acid glycerin, tri (caprylic/capric acid) glycerin, dioleic acid propylene glycol, triisostearic acid glycerin, triisooctanoic acid glycerin, cetyl lactate, myristyl lactate, diisostearyl malate, cyclic alcohol fatty acid ester such as cholesteryl isostearate and cholesteryl 12-hydroxystearate, and the like.

Examples of the metal soap include zinc laurate, zinc myristate, magnesium myristate, zinc palmitate, zinc stearate, aluminum stearate, calcium stearate, magnesium stearate, zinc undecylenate, and the like. Examples of the moisturizing agent include glycerin, propylene glycol, 1,3-butylene glycol, polyethylene glycol, sodium dl-pyrrolidone carboxylate, sodium lactate, sorbitol, sodium hyaluronate, polyglycerin, xylitol, maltitol, and the like.

Examples of the surfactant include anionic surfactants such as higher fatty acid soap, higher alcohol sulfuric acid ester. N-acylglutamic acid salt, and phosphoric acid ester salt; cationic surfactants such as an amine salt and a quaternary ammonium salt; amphoteric surfactants such as betaine type, amino acid type, imidazoline type, and lecithin; and nonionic surfactants such as fatty acid monoglyceride, propylene glycol fatty acid ester, sorbitan fatty acid ester, sucrose fatty acid ester, polyglycerin fatty acid ester, and ethylene oxide condensate.

Examples of the polymer compound include natural polymer compounds such as gum arabic, tragacanth gum, guar gum, locust bean gum, karaya gum, iris moss, quince seed, gelatin, shellac, rosin, and casein; semisynthetic polymer compounds such as carboxymethylcellulose sodium, hydroxyethylcellulose, methylcellulose, ethylcellulose, sodium alginate, ester gum, nitrocellulose, hydroxypropylcellulose, and crystalline cellulose; and synthetic polymer compounds such as polyvinyl alcohol, polyvinylpyrrolidone, sodium polyacrylate, carboxyvinyl polymer, polyvinyl methyl ether, polyamide resin, silicone oil, and resin particles such as nylon particles, methyl polymethacrylate particles, crosslinked polystyrene particles, silicone particles, urethane particles, polyethylene particles, and silica particles.

Examples of the coloring material raw material include inorganic pigments such as iron oxide, ultramarine blue pigment, Prussian blue pigment, chromium oxide, chromium hydroxide, carbon black, manganese violet, titanium oxide, zinc oxide, talc, kaolin, mica, calcium carbonate, magnesium carbonate, isinglass, aluminum silicate, barium silicate, calcium silicate, magnesium silicate, silica, zeolite, barium sulfate, baked calcium sulfate (calcined gypsum), calcium phosphate, hydroxyapatite, and ceramic powder; and tar dyes such as azo-based tar dye, nitro-based tar dye, nitroso-based tar dye, xanthene-based tar dye, quinoline-based tar dye, anthraquinoline-based tar dye, indigo-based tar dye, triphenylmethane-based tar dye, phthalocyanine-based tar dye, and pyrene-based tar dye.

Herein, a powder raw material such as the above-mentioned polymer compound and coloring material raw material may have been surface-treated in advance. As a surface treating method, the previously known surface treating technique can be utilized. Examples thereof include treating methods such as oil solution treatment with a hydrocarbon oil, an ester oil, lanolin or the like, silicone treatment with dimethylpolysiloxane, methylhydrogenpolysiloxane, methylphenylpolysiloxane or the like, fluorine compound treatment with perfluoroalkyl group-containing ester, perfluoroalkylsilane, perfluoropolyether, a polymer having a perfluoroalkyl group or the like, silane coupling agent treatment with 3-methacryloxypropyltrimethoxysilane, 3-glycidoxypropyltrimethoxysilane or the like, titanium coupling agent treatment with isopropyltriisostearoyl titanate, isopropyltris(dioctyl pyrophosphate) titanate or the like, metal soap treatment, amino acid treatment with acylglutamic acid or the like, lecithin treatment with hydrogenated yolk lecithin or the like, collagen treatment, polyethylene treatment, moisturizing treatment, inorganic compound treatment, and mechanochemical treatment.

Examples of the perfume include natural perfumes such as a lavender oil, a peppermint oil, and a lime oil; and synthetic perfumes such as ethylphenyl acetate, geraniol, and p-tert-butylcyclohexyl acetate. Examples of the antiseptic and bactericide include methylparaben, ethylparaben, propylparaben, benzalkonium, benzethonium, and the like.

Examples of the antioxidant include dibutylhydroxytoluene, butylhydroxyanisole, propyl gallate, tocopherol, and the like. Examples of the ultraviolet absorbing agent include inorganic absorbing agents such as fine particle titanium oxide, fine particle zinc oxide, fine particle cerium oxide, fine particle iron oxide, and fine particle zirconium oxide; and organic absorbing agents such as a benzoic acid-based absorbing agent, a para-aminobenzoic acid-based absorbing agent, an anthranilic acid-based absorbing agent, a salicylic acid-based absorbing agent, a cinnamic acid-based absorbing agent, a benzophenone-based absorbing agent, and a dibenzoylmethane-based absorbing agent.

Examples of the special blending ingredient include hormones such as estradiol, estrone, ethinylestradiol, cortisone, hydrocortisone, and prednisone; vitamins such as vitamin A, vitamin B, vitamin C, and vitamin E; skin astringents such as citric acid, tartaric acid, lactic acid, aluminum chloride, potassium aluminum sulfate, aluminum chlorohydroxy allantoinate, zinc paraphenolsulfonate, and zinc sulfate; hair growth promoters such as Cantharides tincture, *capsicum* tincture. Ginger tincture, *Swertia japonica* extract, garlic extract, hinokitiol, carpronium chloride, pentadecanoic acid glyceride, vitamin E, estrogen, and a photosensitizer; whitening agents such as phosphoric acid-magnesium L-ascorbate, and kojic acid; and the like.

EXAMPLES

The present invention will be more specifically illustrated below by way of Examples, but the present invention is not limited to them. First, measuring methods and evaluating methods in Examples and Comparative Examples will be illustrated.

(Measurement of Crystallization Degree, Crystallization Temperature (Maximum Peak Value of Endothermic Peak), Crystal Melting Heat Amount, Crystal Melting Heat Amount Ratio)

Measurement is performed by the method described in JIS K7122: 2012 "Testing Methods for Heat of Transitions of Plastics". It is to be noted that a sampling method and the temperature condition are as follows. A DSC curve is obtained, when about 10 mg of a sample is filled into a bottom of a measurement container made of aluminum without gaps, and retained at 30° C. for 2 minutes under a nitrogen gas flow rate of 20 mL/min, and a temperature is raised from 30° C. to 290° C. at a speed of 10° C./min, using a differential scanning calorimeter DSC6220 Type (manufactured by SII Nano Technology Inc.). As a standard substance, alumina is used.

The crystallization degree calculated in the present invention is the ratio which is obtained by dividing a difference between a melting heat amount (J/g) obtained from an area of a melting peak and a crystallization heat amount (J/g) obtained from an area of a crystallization peak, by a theoretical melting heat amount of 140.1 J/g of a polyethylene terephthalate perfect crystal.

The melting heat amount and the crystallization heat amount are calculated using the analysis software attached to the device.

Specifically, the melting heat amount is calculated from a part surrounded with a straight line connecting a point at which a DSC curve leaves from a baseline on a low temperature side, and a point at which the DSC curve returns again to a baseline on a high temperature side, and the DSC curve. The crystallization heat amount is calculated from an area of a part surrounded with a straight line connecting a point at which a DSC curve leaves from a baseline on a low temperature side, and a point at which the DSC curve returns again to a high temperature side, and the DSC curve.

That is, the crystallization degree is obtained by the following formula.

Crystallization degree (%)=((melting heat amount (J/g)−crystallization heat amount (J/g))/140.1 (J/g))×100

Concerning the partial melting heat amount, in the case where at least two or more peaks exist in the resulting melting peak, a boundary line is provided based on an upwardly convex peak top temperature existing m the melting peak, and each area which is obtained by dividing the melting heat amount into a high temperature side and a low temperature side from the boundary line (partial melting heat amount) is read.

(Measurement of Volume Average Particle Diameter)

The volume average particle diameter of polymer particles is measured with Coulter Multisizer™ 3 (measuring apparatus manufactured by Beckman Coulter, Inc). Measurement is performed using an aperture which was calibrated according to Multisizer™ 3 user's manual published by Beckman Coulter, Inc.

In addition, selection of an aperture to be used in measurement is appropriately performed as follows. When the supposed volume average particle diameter of resin particles to be measured is 1 µm or more and 10 µm or less, an aperture having a size of 50 µm is selected, when the supposed volume average particle diameter of resin particles to be µm measured is greater than 10 µm and 30 µm or less, an aperture having a size of 100 µm is selected, when the supposed volume average particle diameter of resin particles is greater than 30 µm and 90 µm or less, an aperture having a size of 280 µm is selected, when the supposed volume average particle diameter of resin particles is greater than 90 µm and 150 µm or less, an aperture having a size of 400 µm is selected, and so on. When the volume average particle diameter after measurement is different from the supposed volume average particle diameter, the aperture is changed to an aperture having a proper size, and measurement is performed again.

Additionally, when an aperture having a size of 50 µm has been selected, Current (aperture current) is set at −800 and Gain is set at 4, when an aperture having a size of 100 µm has been selected, Current (aperture current) is set at −1600 and Gain is set at 2, and when apertures having a size of 280 µm and 400 µm have been selected, Current (aperture current) is set at −3200 and Gain is set at 1.

As a sample for measurement, 0.1 g of polymer particles are dispersed in 10 ml of a 0.1% by mass aqueous nonionic surfactant solution using TOUCH MIXER (manufactured by YAMATO SCIENTIFIC CO., LTD., "TOUCH MIXER MT-31") and an ultrasonic cleaner (manufactured by VELVO-CLEAR, "ULTRASONICCLEANER VS-150"), and the dispersion is used. The interior of a beaker is mildly stirred in advance during measurement to such a degree that air bubbles do not formulate, and measurement is finished at the time point at which 100 thousands of polymer particles are measured. The volume average particle diameter of polymer particles is an arithmetic average in a particle size distribution based on the volume of 100 thousands of particles.

(Measurement of Intrinsic Viscosity (IV))

The intrinsic viscosity is calculated from the solution viscosity which is obtained by heat-dissolving 0.5 g of a polyethylene terephthalate resin in 100 ml of a tetrachloroethane/phenol=50/50 (wt %/wt %) mixed solution, thereafter, cooling the solution, and measuring the solution viscosity at 25° C.

Example 1

50 grams of pellets of polyethylene terephthalate (product name SA135 manufactured by Mitsui Chemical Inc., IV=0.82 dl/g, crystallization degree 39.4%, specific gravity 1.413) as a polyester-based raw material resin and 100 g of 3-methoxy-3-methyl-1-butanol (product name SOLFIT, manufactured by Kuraray Co. Ltd.) as a glycol ether-based solvent were placed into an autoclave with a stirrer having a volume of 300 ml, and stirred for 2 hours under the condition of 185° C. After 2 hours, the contents were rapidly cooled to room temperature, and made to pass through filtration, washing with water, and drying in an oven at 80° C. to obtain 49 g of pellets of a polyester-based raw material resin which had contacted with the solvent. Decrease in the mass before and after this treatment was seen little, and a surface of pellets after drying was observed with a scanning electron microscope, a porous shape was not observed, and it was confirmed that partial depolymerization had not occurred. IV of pellets of the polyester-based raw material resin which had contacted with the solvent was 0.41 dl/g (reduced to 50%), and the crystallization degree was 38.1% (reduced to 97%).

The resulting contacted polyester-based raw material resin was coarsely ground with Labo Milser (OSAKA CHEMICAL Co. Ltd., small grinding machine Labo Milser PLUS LMPLUS), and thereafter, fine grinding-treated with a current jet mill CJ-10 (grinding pneumatic pressure 0.5 MPa) manufactured by Nisshin Engineering Inc., and as a result, fine polyester-based resin particles having a volume average particle diameter of 7.5 µm were obtained.

Figure 1:
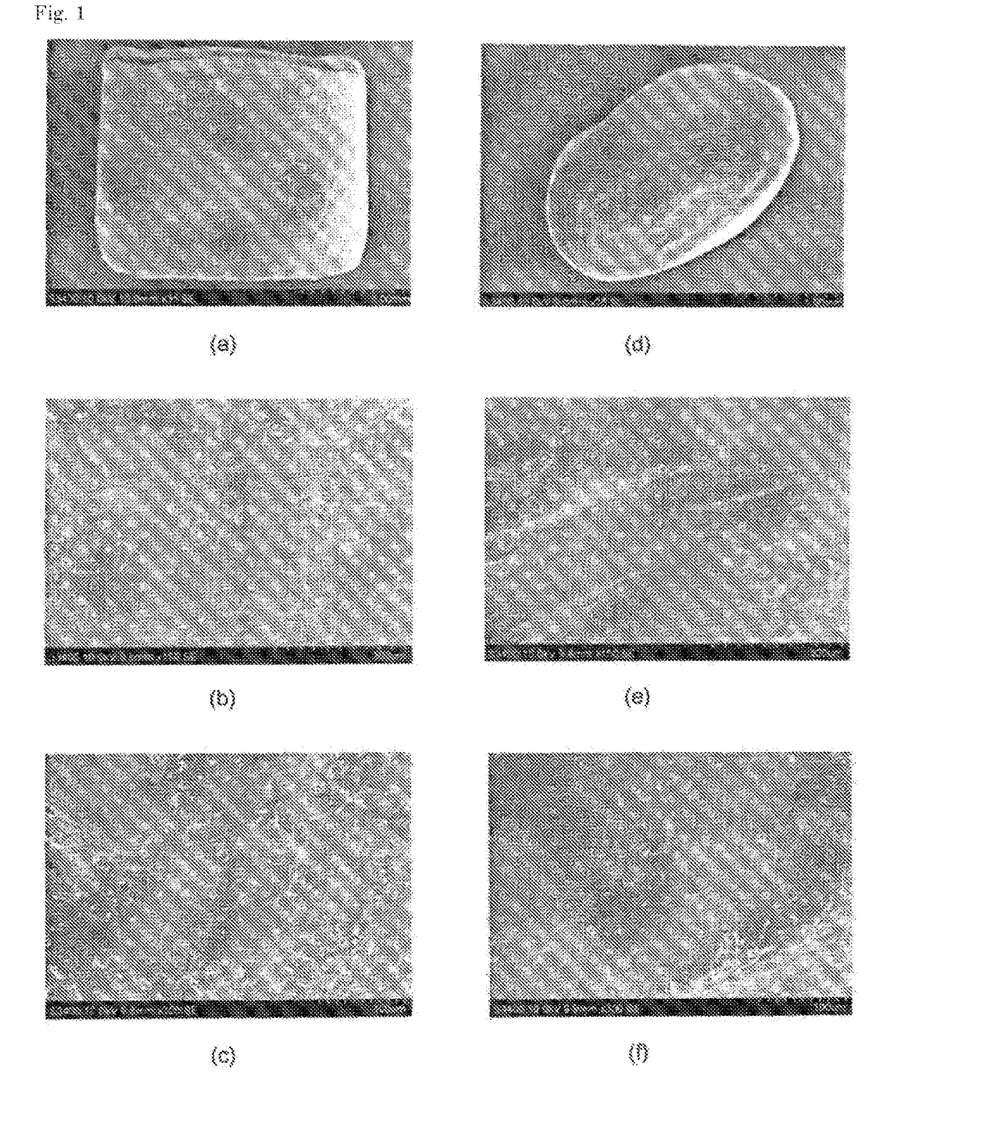
FIG. 1 is electron micrographs of pellets of a polyester-based raw material resin which has contacted with a solvent, of Example 1.

Electron micrographs of pellets of the polyester-based raw material resin which has contacted with a solvent are shown in FIGS. 1(a) to (f). FIGS. 1(a) and (d) show photographs (magnification 35) of a rectangular pellet and a circular pellet in the pellets, respectively. FIG. 1(b) and FIG. 1(c) show photographs of FIG. 1(a) at magnification 150 and magnification 300. FIG. 1(e) and FIG. 1(f) show photographs of FIG. 1(d) at magnification 150 and magnification 300. These photographs show that particles have not become porous. Accordingly, it is seen that polyester-based resin particles are not obtained by grinding through porous pellets.

Example 2

According to the same manner as that of Example 1 except that a temperature at the time of stirring was changed from 185° C. to 175° C., polyester-based resin particles were obtained. IV of pellets of the polyester-based raw material resin which had contacted with a solvent was 0.55 dl/g (reduced to 67%), and the crystallization degree was 40.8% (increased to 104%).

The resulting contacted polyester-based raw material resin was coarsely ground with Labo Milser (OSAKA CHEMICAL Co. Ltd., small grinding machine Labo Milser PLUS LMPLUS), and thereafter, fine grinding-treated with a current jet mill CJ-10 (grinding pneumatic pressure 0.5 MPa) manufactured by Nisshin Engineering Inc., and as a result, fine polyester-based resin particles having a volume average particle diameter of 15.8 µm were obtained.

Example 3

According to the same manner as that of Example 1 except that a temperature at the time of stirring was changed from 185° C. to 175° C., and a stirring time was changed from 2 hours to 8 hours, polyester-based resin particles were obtained. IV of pellets of the polyester-based raw material resin which had contacted with a solvent was 0.22 dl/g (reduced to 27%), and the crystallization degree was 38.6% (reduced to 98%).

The resulting contacted polyester-based raw material resin was coarsely ground with Labo Milser (OSAKA CHEMICAL Co. Ltd. small grinding machine Labo Milser PLUS LMPLUS), and thereafter, fine grinding-treated with a current jet mill CJ-10 (grinding pneumatic pressure 0.5

MPa) manufactured by Nisshin Engineering Inc., and as a result, fine polyester-based resin particles having a volume average particle diameter of 10.9 μm were obtained.

Example 4

According to the same manner as that of Example 1 except that a temperature at the time of stirring was changed from 185° C. to 170° C. polyester-based resin particles were obtained (specific gravity 1.406). In addition, grinding of polyester-based resin particles which had contacted with a solvent was slightly difficult as compared with other Examples. IV of pellets of the polyester-based raw material resin which had contacted with a solvent was 0.70 dl/g (reduced to 85%), and the crystallization degree was 39.6% (increased to 101%).

The resulting contacted polyester-based raw material resin was coarsely ground with Labo Milser (OSAKA CHEMICAL Co., Ltd., small grinding machine Labo Milser PLUS LMPLUS), and thereafter, fine grinding-treated with a current jet mill CJ-10 (grinding pneumatic pressure 0.5 MPa) manufactured by Nisshin Engineering Inc., and as a result, fine polyester-based resin particles having a volume average particle diameter of 45.9 μm were obtained.

Example 5

50 grams of pellets of polyethylene terephthalate (product name CH-611 manufactured by Far Eastern Textile Ltd., IV=1.04 dl/g, crystallization degree 42.8%, specific gravity 1.415) as a polyester-based raw material resin, and 100 g of 3-methoxy-3-methyl-1-butanol (product name SOLFIT, manufactured by KURARAY CO., LTD.) as a glycol ether-based solvent were placed into an autoclave with a stirrer having a volume of 300 ml, and stirred for 5 hours under the condition of 185° C. After 5 hours, the contents were rapidly cooled to room temperature, and made to pass through filtration, washing with water, and drying in an oven at 80° C., to obtain 49 g of pellets of a polyester-based raw material resin which had contacted with a solvent. IV of pellets of the polyester-based raw material resin which had contacted with a solvent was 0.74 dl/g (reduced to 73%), and the crystallization degree was 39.1% (reduced to 91%).

The resulting contacted polyester-based raw material resin was coarsely ground with Labo Milser (small grinding machine Labo Milser PLUS LMPLUS manufactured by OSAKA CHEMICAL Co., Ltd.), and thereafter, fine grinding-treated with a fine grinding device Pulverizer ACM-15H Type manufactured by Hosokawa Micron Corporation, and as a result, fine polyester-based resin particles having a volume average particle diameter of 42.2 gum were obtained.

DSC curves of each of the polyester-based raw material resins used in Examples 1 to 4 and 5 (FIGS. 2 and 3), the polyester-based resin particles of Example 1, the polyester-based resin particles of Example 2, the polyester-based resin particles of Example 3, the polyester-based resin particles of Example 4, and the polyester-based resin particles of Example 5 are shown in FIGS. 4 to 8.

Figure 2:
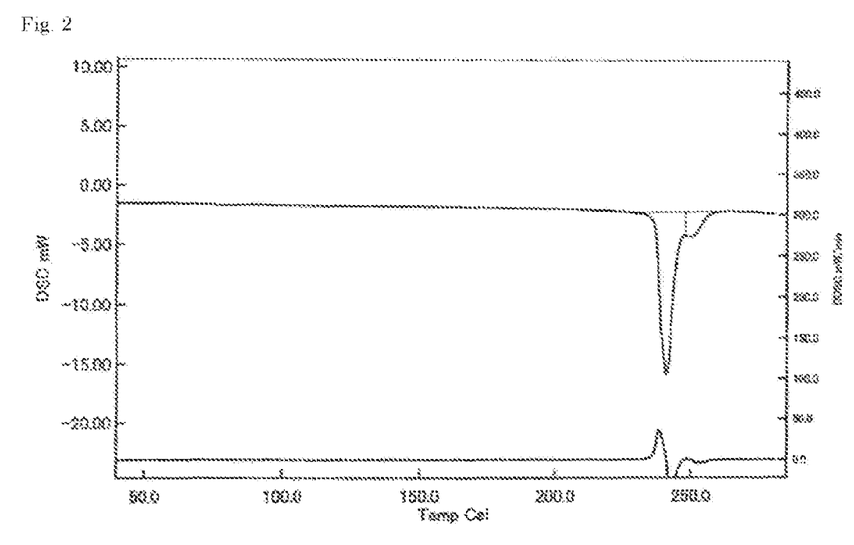
FIG. 2 is a DSC chart of a polyester-based raw material resin of Examples 1 to 4.

In FIG. 2, it is shown that two peaks exist at 241.1° C. and 247.8° C., the crystal melting heat amount of the former is 47.33 J/g, the crystal melting heat amount of the latter is 7.87 J/g, and the crystal melting heat amount ratio is 6.01 (polyester-based raw material resins used in Examples 1 to 4).

Figure 3:
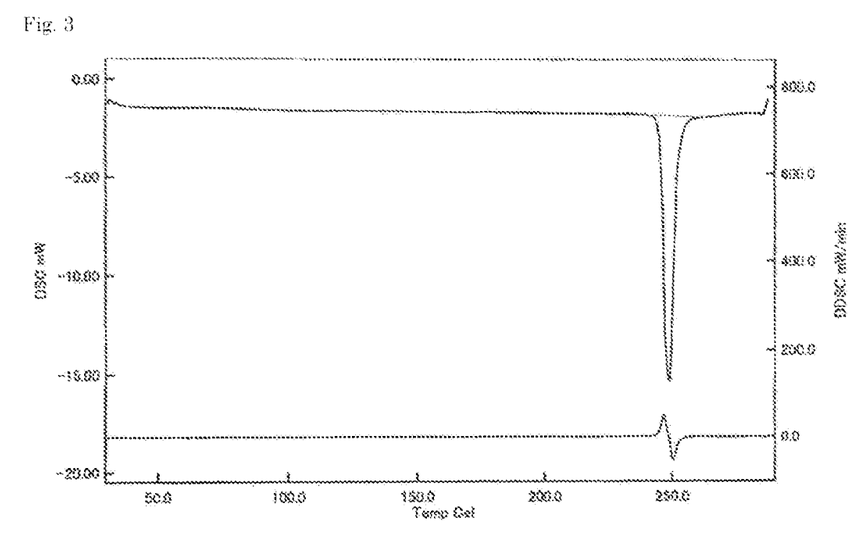
FIG. 3 is a DSC chart of a polyester-based raw material resin of Example 5

In FIG. 3, it is shown that one peak exists at 248.7° C., and the crystal melting heat amount is 58.7 J/g (polyester-based raw material resin used in Example 5).

Figure 4:
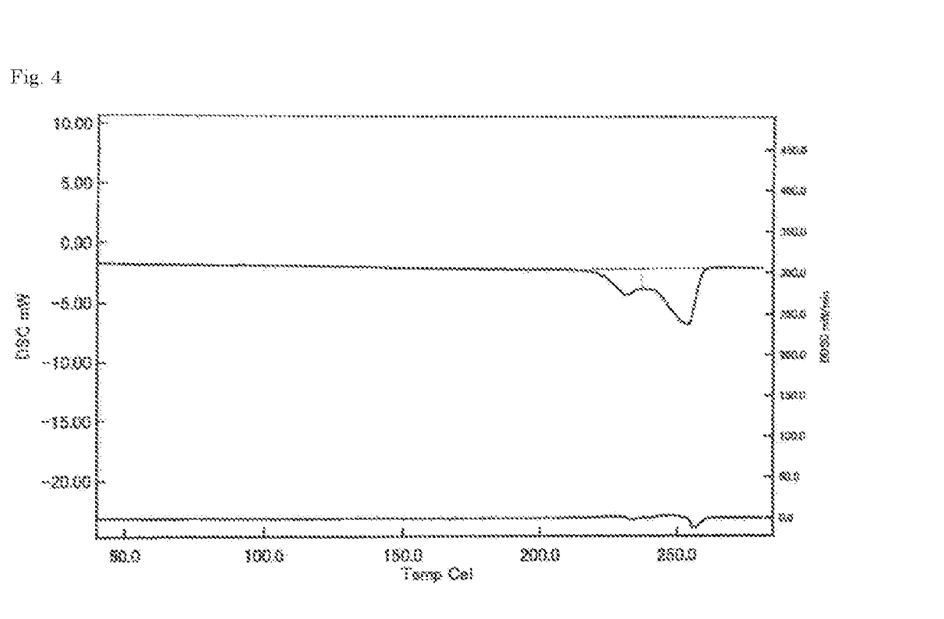
FIG. 4 is a DSC chart of polyester-based resin particles of Example 1.

In FIG. 4, it is shown that two peaks exist at 237.0° C. and 254.0° C., the crystal melting heat amount of the former is 14.87 J/g, the crystal melting heat amount of the latter is 38.56 J/g, and the crystal melting heat amount ratio is 0.386 (Example 1).

Figure 5:
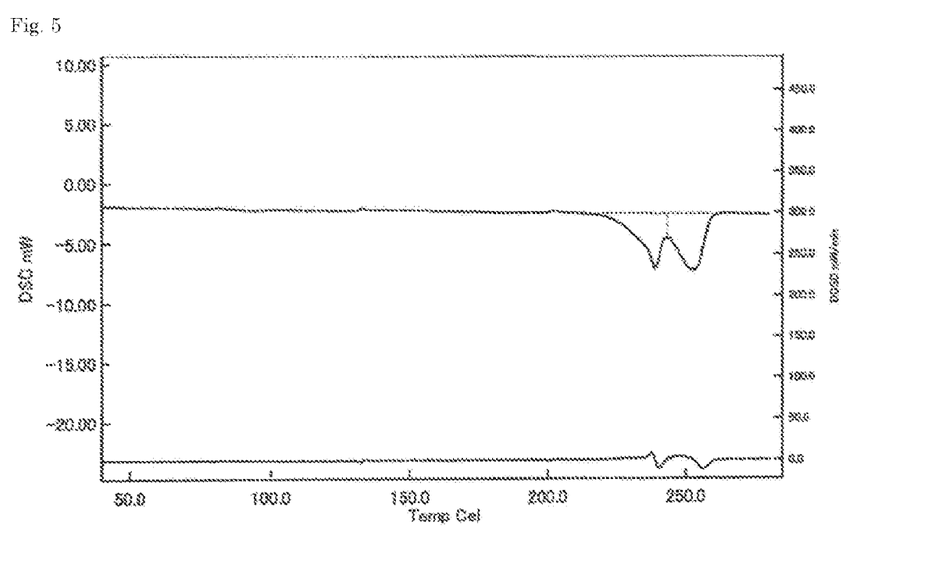
FIG. 5 is a DSC chart of polyester-based resin particles of Example 2.

In FIG. 5, it is shown that two peaks exist at 238.9° C. and 253.0° C., the crystal melting heat amount of the former is 26.68 J/g, the crystal melting heat amount of the latter is 30.50 J/g, and the crystal melting heat amount ratio is 0.875 (Example 2).

Figure 6:
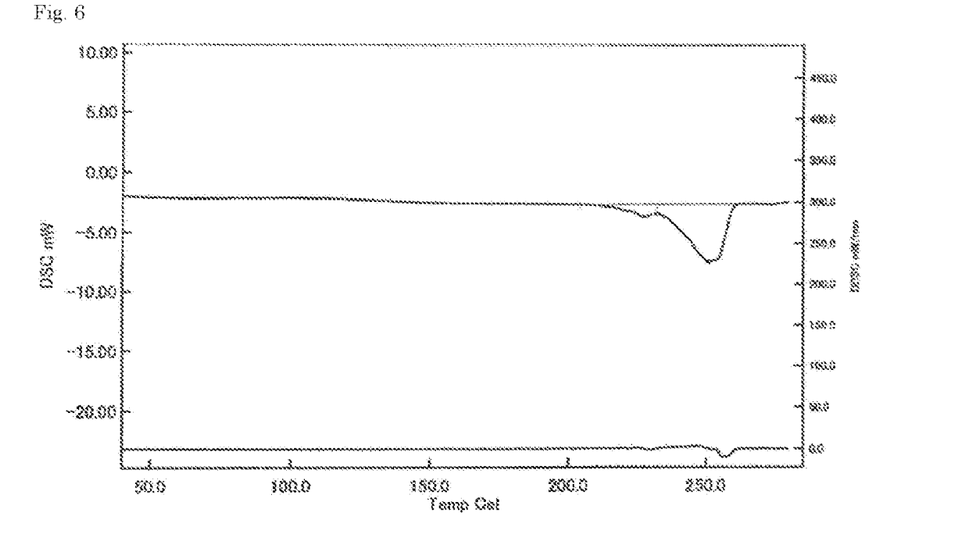
FIG. 6 is a DSC chart of polyester-based resin particles of Example 3.

In FIG. 6, it is shown that two peaks exist at 232.1° C. and 251.0° C., the crystal melting heat amount of the former is 7.093 J/g, the crystal melting heat amount of the latter is 47.03 J/g, and the crystal melting heat amount ratio is 0.151 (Example 3).

Figure 7:
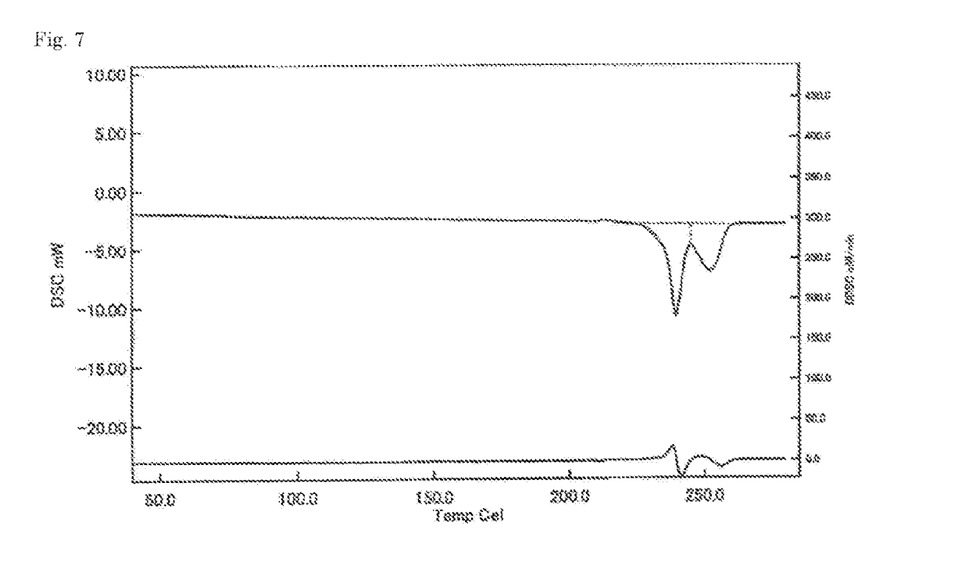
FIG. 7 is a DSC chart of polyester-based resin particles of Example 4.

In FIG. 7, it is shown that two peaks exist at 239.6° C. and 252.3° C., the crystal melting heat amount of the former is 32.06 J/g, the crystal melting heat amount of the latter is 23.39 J/g, and the crystal melting heat amount ratio is 1.371 (Example 4).

Figure 8:
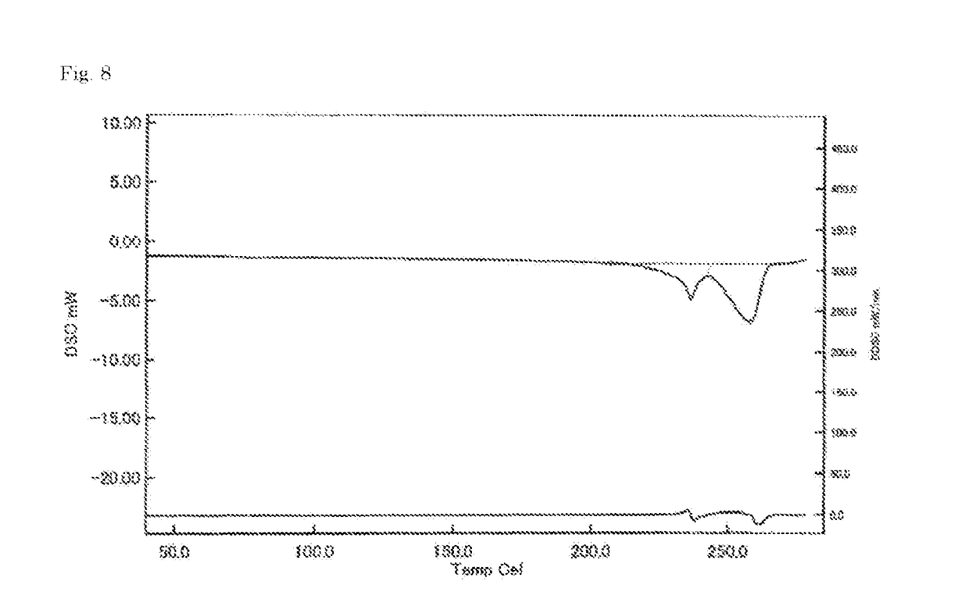
FIG. 8 is a DSC chart of polyester-based resin particles of Example 5.

In FIG. 8, it is shown that two peaks exist at 236.8° C. and 258.0° C., the crystal melting heat amount of the former is 17.72 J/g, the crystal melting heat amount of the latter is 37.09 J/g, and the crystal melting heat amount ratio is 0.478 (Example 5).

Comparative Examples 1 to 3

According to the same manner as that of Example 1 except that the glycol ether-based solvent was changed to propylene glycol monomethyl ether (Comparative Example 1), propylene glycol propyl ether (Comparative Example 2), and propylene glycol butyl ether (Comparative Example 3), respectively, a polyester-based raw material resin was contacted with the solvent.

The polyester-based raw material resin after contact was coarse grinding-treated with Labo Milser, but could not be ground in any case.

Production Examples of Coating Material

Paint Production Examples 1 and 2

2 parts by mass of each resin particles obtained in Examples 1 and 2, and 20 parts by mass of a commercially available aqueous acrylic-based glossy paint (manufactured by Kanpe Hapio Co., Ltd., product name Super Hit) were mixed for 3 minutes and degassed for 1 minute using a stirring degassing device, thereby, a paint was obtained.

The resulting paint was coated on an ABS resin (acrylonitrile-butadiene-styrene resin) plate using a coating device set with a blade of the clearance 75 μm, and dried, thereby, a coated film was obtained. The gloss (60°) which was obtained by measuring the resulting coated film using GLOSS CHECKER IG-330 manufactured by HORIBA, Ltd. was 10 and 12, respectively.

Production Example 1 of Coating Material for PET Film 7.5 parts by mass of the resin particles obtained in Example 1, 30 parts by mass of an acrylic resin (manufactured by DIC Corporation, product name ACRYDIC A811), 10 parts by mass of a crosslinking agent (manufactured by DIC Corporation, product name VM-D), and 50 parts by mass of butyl acetate as a solvent were mixed for 3 minutes and degassed for 1 minute using a stirring degassing device, thereby, a coating liquid was obtained.

The resulting coating liquid was coated on a PET film having a thickness of 125 μm using a coating device set with a blade of the clearance 50 μm, and dried at 70° C. for 10 minutes, thereby, a film was obtained. The haze of the resulting film was 79.6%, and the total light transmittance was 88.8%.

Production Example 2 of Coating Material for PET Film 5 parts by mass of the resin particles obtained in Example 1, 85 parts by mass of pentaerythritol triacrylate (manufactured by KYOEISHA CHEMICAL Co., Ltd., product name: PE-3A) as a photopolymerizable polyfunctional polymer, 0.5 parts by mass of 1-hydroxycyclohexyl phenyl ketone (product name "Irgacure (registered trademark) 184", manufactured by BASF Japan Ltd.) as a photoradical polymerization initiator, and 68 parts by mass of toluene as a solvent were mixed for 3 minutes and degassed for 1 minute using a stirring degassing device, thereby, a coating liquid was obtained.

The resulting coating liquid was coated on a PET film (thickness 125 μm) as a transparent substrate with a bar coater No. 07 (manufactured by Daiichi Rika Co., Ltd.), the coated coating liquid was dried at 80° C. over 1 minute, and then, this coated layer was irradiated with an ultraviolet ray for 5 minutes with an ultraviolet irradiating device of ultraviolet illuminance of 3 W/cm$^2$, thereby, the dried coated layer was cured to prepare a coated film. The haze of the resulting film was 19.4%, and the total light transmittance was 90.1%.

Formulation Example of Cosmetic Material

Blending Example 1

| Production of Powder Foundation Blending Amount | |
| --- | --- |
| Resin particles obtained in Example 1 | 10.0 parts by mass |
| Red iron oxide | 3.0 parts by mass |
| Yellow iron oxide | 2.5 parts by mass |
| Black iron oxide | 0.5 parts by mass |
| Titanium oxide | 10.0 parts by mass |
| Mica | 20.0 parts by mass |
| Talc | 44.0 parts by mass |
| Liquid paraffin | 5.0 parts by mass |
| Octyldodecyl myristate | 2.5 parts by mass |
| Vaseline | 2.5 parts by mass |
| Antiseptic | proper quantity |
| Perfume | proper quantity |
| Production Method | |

Resin particles, red iron oxide, yellow iron oxide, black iron oxide, titanium oxide, mica, and talc are mixed with a Henschel mixer, a solution obtained by mixing and dissolving liquid paraffin, octyldodecyl myristate, vaseline, and an antiseptic is added thereto, and uniformly mixed. A perfume is added thereto, the materials are mixed, and ground, and made to pass through a sieve. This is compression-molded in a metal dish to obtain a powder foundation.

Blending Example 2

| Production of Cosmetic Milky Lotion Blending Amount | |
| --- | --- |
| Resin particles obtained in Example 1 | 10.0 parts by mass |
| Stearic acid | 2.5 parts by mass |
| Cetyl alcohol | 1.5 parts by mass |
| Vaseline | 5.0 parts by mass |
| Liquid paraffin | 10.0 parts by mass |
| Polyethylene (10 mole) monooleic acid ester | 2.0 parts by mass |
| Polyethylene glycol 1500 | 3.0 parts by mass |
| Triethanolamine | 1.0 part by mass |
| Purified water | 64.5 parts by mass |
| Perfume | 0.5 parts by mass |
| Antiseptic | proper quantity |
| Production Method | |

First, stearic acid, cetyl alcohol, vaseline, liquid paraffin, and polyethylene monooleic acid ester are heated and dissolved, resin particles are added thereto, and the materials are mixed, and retained at 70° C. (oily phase). Separately, polyethylene glycol and triethanolamine are added to purified water, the materials are heated and dissolved, and retained at 70° C. (aqueous phase). The oily phase is added to the aqueous phase, pre-emulsification is performed, thereafter, the pre-emulsification product is uniformly emulsified with a homomixer, and after emulsification, the emulsion is cooled to 30° C. while stirring, thereby, a cosmetic milky lotion is obtained.

What is claimed is:

1. Polyester-based resin particles comprising a polyester-based resin as a base resin,
   wherein
   said base resin exhibits a plurality of endothermic peaks corresponding to crystal melting temperatures by DSC measurement,
   at least one of said endothermic peaks exists in each region of a low temperature side region and a high temperature side region,
   a maximum endothermic peak of said low temperature side region and a maximum endothermic peak of said high temperature side region exhibit a crystal melting heat amount ratio (low temperature side crystal melting heat amount/high temperature side crystal melting heat amount) in a range of 0.1 to 1.5, said polyester-based resin particles have a volume average particle diameter of 1 to 50 μm, and said polyester-based resin particles have a crystallization degree of 30 to 50% and do not contain thread-like particles.

2. The polyester-based resin particles according to claim 1, wherein said polyester-based resin is polyethylene terephthalate.

3. The polyester-based resin particles according to claim 1, wherein the maximum endothermic peak of said low temperature side region exhibits a maximum peak value at a range of 230° C. or higher and lower than 250° C., and the maximum endothermic peak of said high temperature side region exhibits a maximum peak value at a range of higher than 250° C. and 260° C. or lower.

4. The polyester-based resin particles according to claim 1, wherein the maximum endothermic peak of said low temperature side region exhibits a crystal melting heat amount of 5 to 35 J/g, and the maximum endothermic peak of said high temperature side region exhibits a crystal melting heat amount of 20 to 50 J/g.

5. A method for producing the polyester-based resin particles as defined in claim 1, comprising the steps of:

contacting a polyester-based raw material resin having an intrinsic viscosity of 0.5 to 1.3 dl/g and a crystallization degree by DSC measurement of 30 to 50%, with a glycol ether-based solvent; and grinding a mixture after the contact, wherein said contact is performed under a temperature of a crystallization temperature of a polyester-based raw material resin or higher, and said glycol ether-based solvent is 3-methoxy-3-methyl-1-butanol.

6. A coating material blending with the polyester-based resin particles as defined in claim 1.

7. A cosmetic material blending with the polyester-based resin particles as defined in claim 1.

* * * * *